United States Patent [19]
Kalidindi

[11] Patent Number: 5,440,941
[45] Date of Patent: * Aug. 15, 1995

[54] MULTIPLE-SAMPLE SEGMENTED SAMPLING DEVICE AND METHOD OF USE

[76] Inventor: Sanyasi R. Kalidindi, 8303 Hana Rd., Edison, N.J. 08817

[ * ] Notice: The portion of the term of this patent subsequent to Aug. 16, 2011 has been disclaimed.

[21] Appl. No.: 239,420

[22] Filed: May 6, 1994

Related U.S. Application Data

[63] Continuation-in-part of Ser. No. 70,281, Jun. 1, 1993, Pat. No. 5,337,620.

[51] Int. Cl.⁶ .............................................. G01N 1/12
[52] U.S. Cl. .................................................. 73/864.64
[58] Field of Search ..................... 73/864.63–864.67, 73/863.31

[56] References Cited

U.S. PATENT DOCUMENTS

| | | |
|---|---|---|
| 2,185,651 | 1/1940 | Sollie . |
| 2,875,615 | 3/1959 | Ulvin . |
| 3,080,760 | 3/1963 | Piersma . |
| 4,660,423 | 4/1987 | Armstrong et al. . |
| 4,744,256 | 5/1988 | Niskin . |
| 4,790,198 | 12/1988 | Awtry et al. . |
| 5,337,620 | 8/1994 | Kalidini ............... 73/864.64 |

FOREIGN PATENT DOCUMENTS 484331  11/1954  Italy .

*Primary Examiner*—Robert Raevis
*Attorney, Agent, or Firm*—Richard C. Litman

[57] ABSTRACT

A multiple-sample sampling and measuring device which may be extended and a method of using the device. Dies defining sampling cavities of varying volumes nest within receiving rod segments which, in turn, nest in tubular casing segments. The casing segments have aligned apertures corresponding to preferred die locations. These casing segments are series connected, and the device is dipped into the mixture being sampled. Various die arrangements are disclosed. The distal end of the device has a solid cone and the proximate end of the device has a handle to rotate the connected receiving rod and dies to obtain accurate volumetric sampling of pharmaceutical powders, foods, ointments, cosmetic creams and the like.

19 Claims, 4 Drawing Sheets

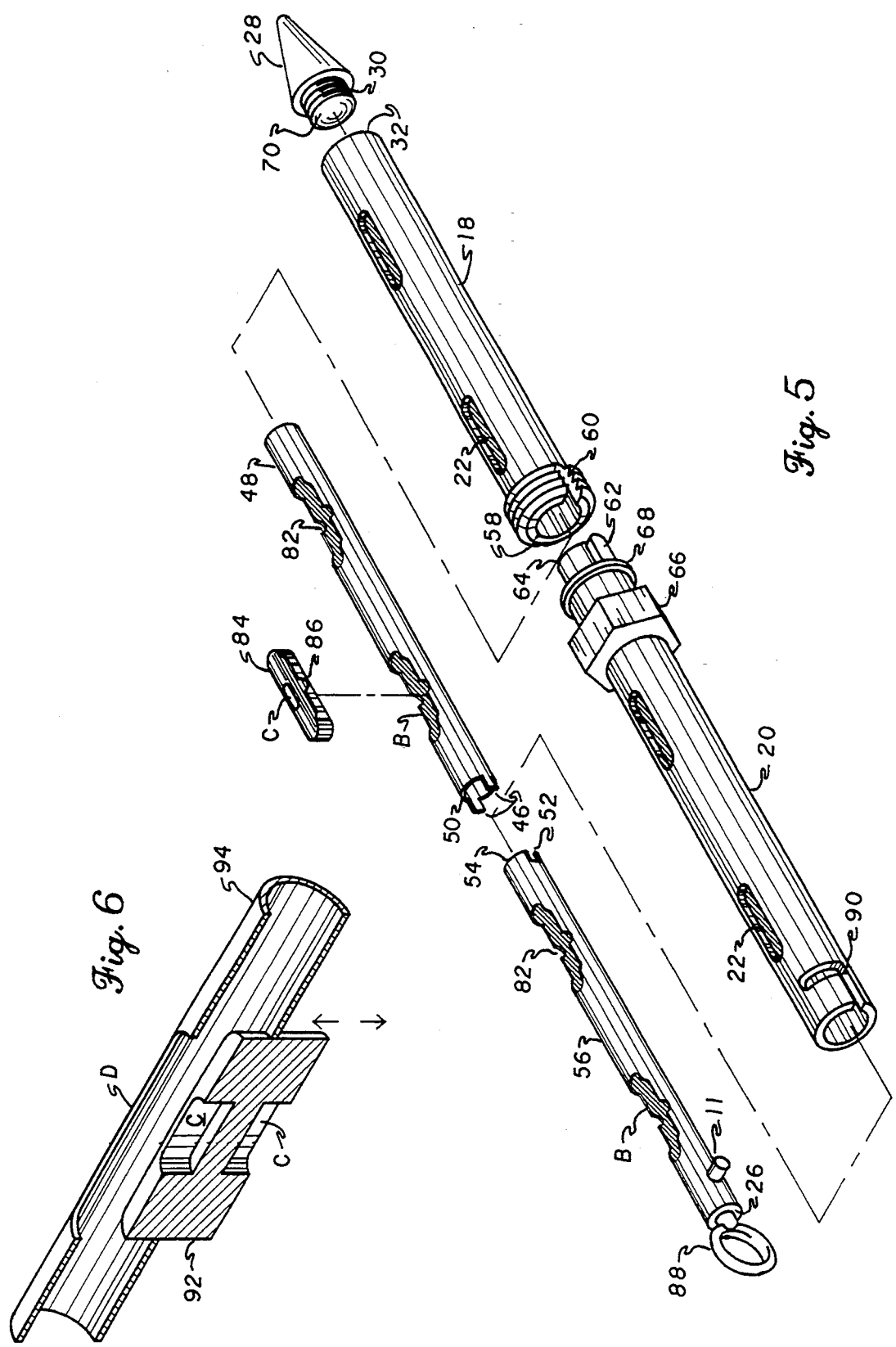

MULTIPLE-SAMPLE SEGMENTED SAMPLING DEVICE AND METHOD OF USE

REFERENCE TO RELATED APPLICATION

This is a continuation-in-part of application Ser. No. 08/070,281, filed Jun. 2, 1993, entitled "Sampling Tool And Method Of Use", and now U.S. Pat. No. 5,337,620.

BACKGROUND OF THE INVENTION

1. Field of the Invention

The present invention relates to a sampling device or tool and a method for using said device in taking precise sample volumes in duplicate, triplicate and/or quadruplicate, of powder blends or emulsion mixtures at various depths simultaneously by utilizing dies with varying sample volumes. This device enables the procurement of these samples from very large blenders or containers by providing a segmented sampler design.

2. Description of the Prior Art

In the manufacture of solid dosage form pharmaceutical solids and semi-solid dosage forms, one of the critical processing steps is the blending of the active ingredient(s) with the inactive ingredient(s) in a blender or mixer. Before further processing of such mixtures, samples are taken from different areas of these mixtures and analyzed to check whether or not the active ingredient is uniformly distributed. Such a test is called a content uniformity test or a homogeneity test. Whenever a powder or a semi-solid mixture is tested for homogeneity, the test results would be influenced by the sample size and the sampling technique. In order to insure accurate testing, the sample size should be as close to the unit dose as possible; and the sampling technique should be such that the mixture is minimally disturbed during sampling. However, unit-dose sampling of mixtures with varying dosages and bulk densities requires multiple sampling devices. The other factors that compound this problem are the large range of mixer sizes, limited clearance between the top of the mixer and the ceiling, the large number of samples to be taken, the necessity for a duplicate, triplicate or quadruplicate set of samples, the requirement of thorough cleanability of the device, and the necessity of preventing leakage of semi-solid samples. All these factors together impose an economic penalty on the manufacturer.

The present invention overcomes these problems by providing a sampling device that permits the following advantages. (1) Unit-dose sampling is accomplished at various depths of the mixture by using dies of varying volumes. (2) The sampling location in the mixture is readily changed by the use of dummy or blank dies to block any of the sampling locations. (3) The option of taking duplicate, triplicate or quadruplicate samples from exactly the same area at each of the sampling locations is readily made by vertical and/or horizontal movement of only the internal sampling or receiving rod that accommodates two, three or four dies, respectively, at each of the sample cavities. (4) Large blenders/mixers are readily sampled by utilizing the sampling rod and the outer casing in sections that are joined above or within the blender/mixer. (5) Thorough cleaning of the outer casing is enabled by utilizing a removable solid cone tip.

A number of patents have been issued that address sampling of various materials. These patents will be discussed in the order of their perceived relevance to the claimed invention.

In Italian Patent No. 484,331 issued in November, 1954 to Dino Donadon, there is disclosed a sampler of immiscible liquids which consists of an inner tube containing partitioned volumes with apertures for each compartment, an outermost tube, and an intermediate tube with apertures which align with both the inner tube's apertures and corresponding apertures in the outermost tube. A portion of the second tube's apertures contains a filter. The innermost tube and the intermediate tube have separate handles for alignment of their respective apertures with the apertures of the outer tube in order to take samples of an immiscible liquid system. There is no disclosure of dies, facility for duplicate, triplicate or quadruplicate sampling, segmentation of the sampler, a separate cone tip, and the operation of his sampler without the essential intermediate tube and associated filters.

In U.S. Pat. No. 4,790,198 issued on Dec. 13, 1988 to Jon Awtry et al., a grain probe is disclosed having an inner tubular member's openings aligned with the outer tubular member's opening to take grain samples. The grain probe has a pointed end to aid in the penetration of the grain pile. There is no disclosure of individual dies, duplicate to quadruplicate sampling capability, segmentation of the grain probe or the removability of the pointed end.

In U.S. Pat. No. 3,080,760 issued on Mar. 12, 1963 to Henry D. Piersma, there is disclosed a disposable sample probe for bulk chemicals including powder. The probe is a simple two-tube device with alignment of separate cavities with the outer tube's apertures for taking samples. Again, there is no suggestion of the use of individual dies, duplicate to quadruplicate sampling and segmentation of the device.

In U.S. Pat. No. 2,875,615 issued on Mar. 3, 1959 to Orrion A. Ulvin, a grain and seed probe is disclosed which utilizes a spiral element within an apertured outer tube, but without any segmentation of the long probe.

In U.S. Pat. No. 4,744,256 issued on May 17, 1988 to Shale J. Niskin, there is disclosed a non-segmented water sampler device dropped from an airplane to obtain a single sample by utilizing a valving arrangement to open and close the sampler.

In U.S. Pat. No. 2,185,651 issued on Jan. 2, 1940 to John Sollie, there is disclosed a milk sampler including a rod (with a handle) to reduce sample volume capacity.

Finally, in U.S. Pat. No. 4,660,423 issued on Apr. 28, 1987 to John M. Armstrong et al., a water sampling apparatus is disclosed wherein sampling is initiated by in situ puncturing of a sealed tube to obtain one sample.

The prior art discussed in the parent patent is incorporated by reference herein.

None of the above inventions and patents, taken either singly or in combination, is seen to describe the instant invention as claimed.

SUMMARY OF THE INVENTION

The present invention is a multiple-sample, segmented sampling device or tool and a method for utilizing said device for obtaining duplicate, triplicate or quadruplicate samples of precise and selectively variable volumes from different levels in a blender or mixer containing pharmaceutical or food powders, ointments, creams or other semi-solid emulsions in one sampling attempt. Sampling dies having cavities of varying specific volumes are placed within die receiving areas in a receiving rod of a predetermined length. The receiving rod containing the dies is inserted in a tubular casing. The tubular casing has apertures or ports that are slightly smaller than the exposed area size of the dies and are aligned with the locations of the dies on the inserted receiving rod. There is minimal space between the receiving rod and the casing to permit rotational or longitudinal (vertical) movement of the receiving rod and to minimize leakage between samples.

Multiple samples from a single port may be obtained by employing various modifications of the basic device. Multiple sampling cavities may be formed in one die. A die may have sampling cavities located 180 degrees from each other. Alternately, two or three abutting dies may be placed in a line. Finally, multiple dies, each containing a sampling cavity, may be arranged either circumferentially or grouped in a rectangle in a single die holder which occupies the inner volume of a hollow receiving rod.

Accordingly, it is a principal object of the invention to provide a sampling device or tool and a method for its use wherein duplicate, triplicate and/or quadruplicate samples of varying volumes may be obtained from several depths of powder or semi-solid material.

It is another object of the invention to provide a sampling device with blank dies to block some sample ports in order to change the depth of sampling or to reduce the number of samples.

It is an object of the invention to provide springs to support dies to prevent leakage of the samples, which may be necessary with semi-solid materials.

It is a further object of the invention to provide connection means between the receiving rod segments and between the tubular casing segments.

Still another object of the invention is to provide terminal apparatus such as a removable solid cone at the distal end of the sampling device and a removable or fixed handle at the proximate end.

Another object of the invention is to provide positioning means for the handle in the last tubular casing's proximate end to rotate or vary the depth at which the dies are located.

It is a yet another object of the invention to fabricate the device from either stainless steel or plastic materials.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 5 is an exploded perspective view of the third embodiment of a hollow die receiving rod provided with a ringed handle, different dies and different connection means (fingers and grooves).

FIG. 6 is an exploded isometric sectional detail view of the fourth embodiment of a single die containing two sampling cavities at locations positioned 180 degrees from each other in a receiving rod.

Similar reference characters denote corresponding features consistently throughout the attached drawings.

DETAILED DESCRIPTION OF THE PREFERRED EMBODIMENTS

Figure 1:
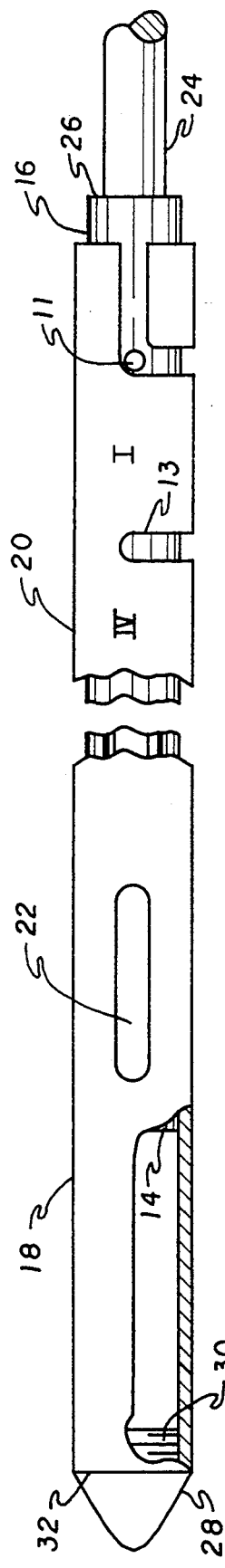
FIG. 1 is a top plan view, partially broken away, of the preferred embodiment of the segmented (not shown) sampling device utilizing solid die receiving rods having a positioning pin cooperating with the groove or slot in the tubular casing which has a sample port or aperture.
Figure 2:
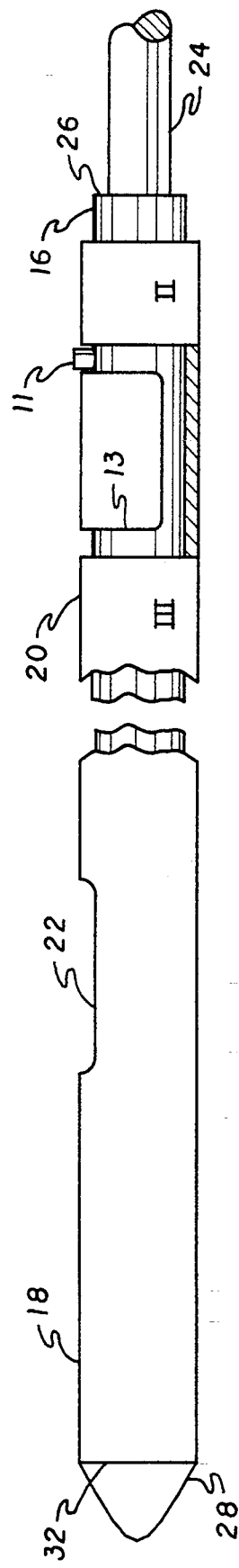
FIG. 2 is a side elevational view of the FIG. 1 sampling device viewed from a vantage point 90 degrees offset from the view of FIG. 1.
Figure 3:
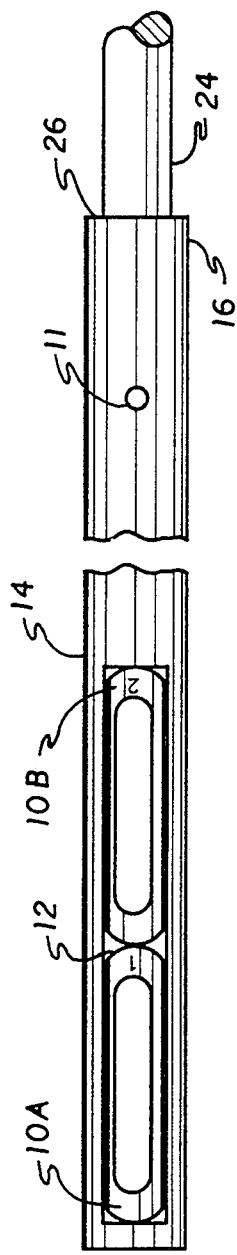
FIG. 3 is a top plan view of the receiving rod of FIG. 1's sampling device showing the receiving rod containing a first cavity holding or nesting two dies arranged longitudinally and the sampling cavities within the dies.

Referring to FIGS. 1, 2 and 3, the preferred embodiment of the sampling device is shown. The device has a plurality of dies 10 arranged in longitudinal formation with only two dies, 10A and 10B, shown in a first cavity 12 of at least two solid die receiving means 14, 16. These receiving means are rod-shaped and encased in at least two sample access means or tubular casings 18, 20 that are hollow tubes having a row of sample ports or apertures 22 (only one is shown in FIG. 1). A handle 24 (only a stem portion is shown) is attached by threading means (not shown) to die receiving means 16 at its proximate end 26. Solid cone 28 is attached by threading means 30 to the distal end 32 of the first tubular casing 18.

The first embodiment in FIG. 3 illustrates two dies 10A and 10B aligned longitudinally in one first cavity 12. These dies have sampling cavities 12 which are filled with the powder mixture one at a time by moving the receiving rod pin 11 from position I in the groove or slot 13 in FIG. 1, a closed die position, to position II in FIG. 2 to fill the cavity of sampling die 10A. By moving to position III in FIG. 2, the second die 10B in FIG. 3 is exposed and filled. When the handle is turned and the pin moved to position IV in FIG. 1, the port 22 is closed and the sampler device may be taken out of the powder mixture to complete the sampling operation.

Figure 4:
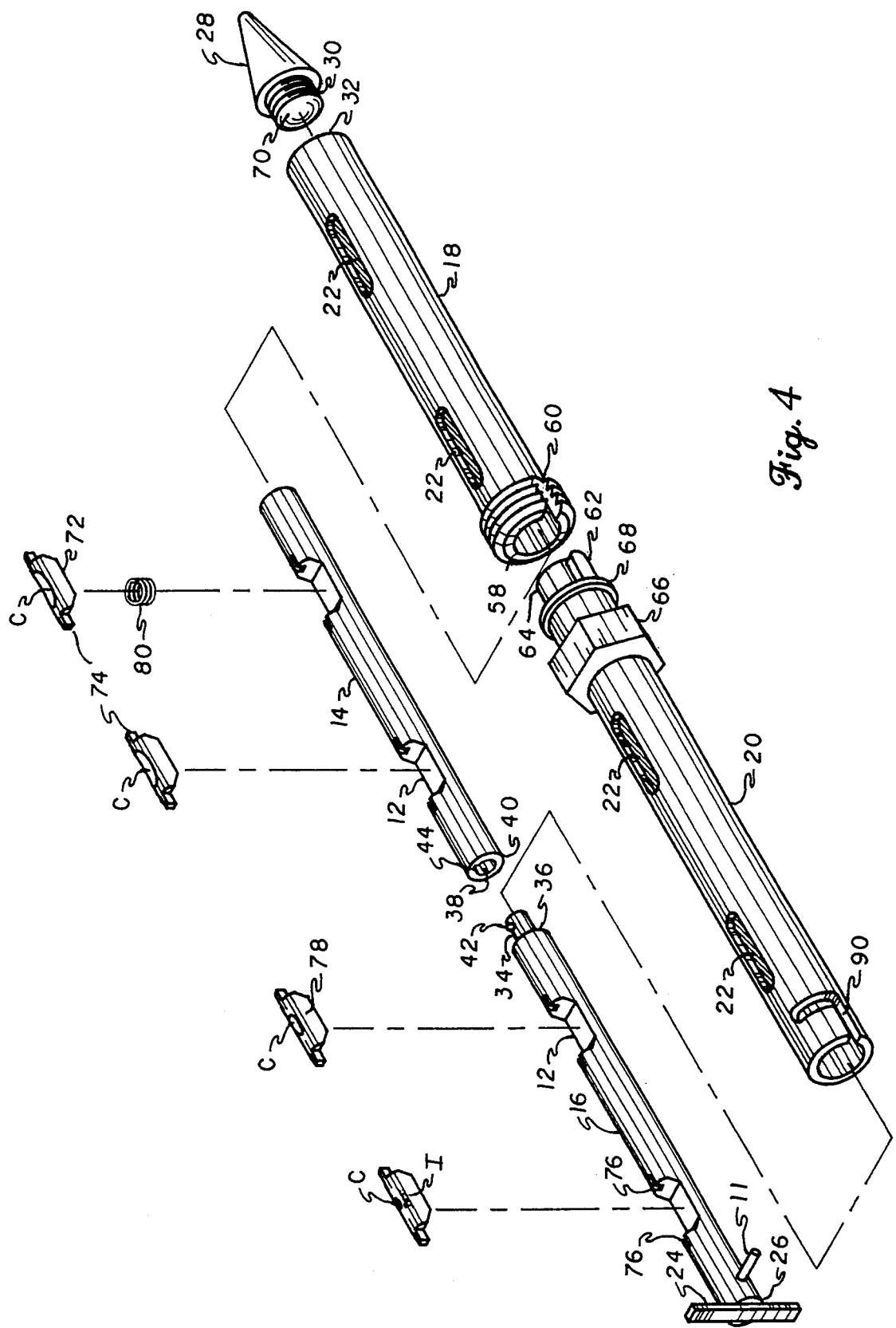
FIG. 4 is an exploded perspective view of the second embodiment of the segmented sampling device utilizing solid die receiving rods joined by socket means and having a handle with straight bars.

Turning now to the second embodiment of FIG. 4, wherein first and second die receiving means are solid rods 14, 16, respectively, which are each preferably a foot long and approximately ¾ inch in diameter. These die receiving means are mutually engageable by a projecting member 34 at the distal end 36 of rod 16 and a socket member engagement means 38 at the proximate end 40 of rod 14. The projecting member 34 has a spring-urged and radially projecting member or peg 42 for interlocking with the socket member 38. The socket member requires a groove 44 or the like for receiving the projecting member 34 and aligning the joined die receiving means or rods 14, 16 and dies 10.

Another alternative modification is illustrated in the exploded view of FIG. 5 wherein interfit of two fingers 46 in the hollow first die receiving rod 48 at its proximate end 50, and two grooves 52 located at the distal end 54 of the hollow second die receiving rod 56, permit the aligned union of die receiving rods 48, 56. A further embodiment of engagement means is the threaded engagement means disclosed in the parent application but not shown in the instant drawings.

In FIGS. 4 and 5, the first tubular casing 18 has an open distal end 32 and an open proximate end 58 with a slot 60 which cooperates with the key 62 at the open distal end 64 of the second tubular casing 20. The locking union nut 66 of tubular casing 20 secures alignment of apertures 22 in both casings by abutting against ridge 68 on the outer surface of and proximate to the distal end 64 of the second tubular casing 20. The open distal end 32 of the first tubular casing 18 is closed by a solid cone tip 28 by engaging external threading 30 on the proximate end 70 of the cone 28 with the internal threading (not shown) in the distal end 32 of the first casing segment 18.

In FIG. 4, it can be seen that the dies 10 have a number of differently sized cavities C. These cavities are dimensioned so that they hold a very precise volume of material to be sampled and tested. The dies also have indicial on their surfaces to show the user the volume that they contain. This volume would preferably be measured in cubic centimeters. In the preferred embodiment, each die 10 has a flat bottom 72 that allows it to be placed on a flat surface, such as a laboratory table or the like, thus minimizing the likelihood of inadvertent spilling of the sample. This bottom 72 matches the flat receiving surface or flat bottomed slot 12 in the die receiving means or rods 14, 16. Additionally, the dies 10 have a pair of ears 74 that are secured in the pair of slots 76 in the die receiving means or rods 14, 16. The cooperation of the ears 74 and the slots 76 prevents lateral movement of the dies 10 when they are placed in the receiving means or rods 14, 16. This configuration also allows for flattened grasping surfaces 78 on the sides of the dies 10 for ease in manipulation of the dies 10 into and out of the receiving means or rods 14, 16. Spring 80 in FIG. 4 is placed between the die 10 and the receiving rod holder 14 or 16 or any other supporting surface to assure a close fit of the die with the tubular casing, and hence, an efficient seal of a die with a tubular casing's aperture 22.

The third embodiment in FIG. 5 illustrates the use of hollow die receiving means or rods 48, 56 having cavities B instead of flat bottomed slots 12 to accept the dies. In this embodiment, hollow tube receivers 48, 56 lack ear slots 76, but include indentations 82 to enable extraction of the dies 84 having shoulders 86 from receivers 48, 56.

Note that though only two die receiving means 14, 16 in FIG. 4 and 48, 56 in FIG. 5 are illustrated, a larger number of these segments may be used, depending on the length of the sampling device desired, or the number of samples that are desired. A total length as long as 12 feet for tubular casings of approximately ⅝ inch to one inch in outside diameter is contemplated for these embodiments. Furthermore, the intermediate segments of the receiving rods and tubular casings for a sampling device having more than two segments would necessarily have the appropriate engagement means for interconnection already disclosed.

Located at the proximate end 26 of the second die receiving means or rod 16 is the manipulable die displacement means which is in the form of a straight bar handle 24 as depicted in FIG. 4. This handle 24 could be permanently attached to the second die receiving means or rod 16 or it could be removable with threaded engagement means (not shown) to make the apparatus more modular. Alternatively, the handle could take the form of a ring handle 88 as shown in FIG. 5, and be either removable (not shown) or permanently attached to the last die receiving rod. Rotation of the die receiving means or rods 48, 56 with the ringed handle 88 especially facilitates the sampling process.

Once the desired sample volumes are chosen and the dies 10, 84 are in place on the first receiving means or rods 14, 48 respectively, the dies and receiving means are inserted in the first sample access means or tubular casing 18 of FIG. 4 or FIG. 5, having an interior wall with a diameter dimensioned to smoothly and snugly receive the dies 10, 84 and the receiving means or rods 14 or 48. The solid cone end 28 functions as a travel stop for the die receiving means, and holds the receiving rods 14 or 48 in a predetermined relationship such that the cavities C and the apertures 22 in the first hollow tube or tubular casing 18 are aligned.

The second segment is connected to a first segment by attaching the second tubular casing 20 to the first tubular casing 18 by the following procedure. Key 62, located at the distal end 64 of tubular casing 20, engages and aligns with slot 60 at the proximate end 58 of the first tubular casing 18, and the joint is secured by urging union nut 66 against ridge 68. Then, the second die receiving means or rod 16 or 56 is joined to the first die receiving means or rod 14 or 48, respectively, by connecting the distal end 36 or 54 of the second die receiving means or rod 16 or 56 respectively, containing more dies 10 or 84 by the following coupling arrangement. Projecting member 34 of solid rod 16 or grooves or slots 52 of hollow rod 56 engage with, respectively, the socket 38 of solid rod 14 or fingers 46 of hollow rod 48. This coupling arrangement maintains the alignment of the apertures or ports 22 in tubular casings 18 and 20.

The last receiving rod may have a permanently attached handle. If the handle is removable and removed from the second or last receiving rod, handle 24 or 88 is added to complete the device.

The die receiving means 14, 16 or 48, 56 containing the dies 10, 84 are then rotated by using the handle 24 or 88, respectively, as illustrated by FIGS. 4 and 5 into a first position in the slot 90, such that the cavities C are misaligned with the apertures or ports 22. The device is now ready to be inserted in a blender (not shown) or a like vessel containing an amount of the fluent mixture which the user is desirous to sample. Examples of suitable fluent mixtures may be in the form of a powder, emulsion or cream of pharmaceutical, cosmetic or food compositions or the like.

Once the sampling device is inserted in the fluent mixture, the handle 24 or 88 is then used to again rotate the die receiving means 14, 16 or 48, 56 and the dies 10, 84 into a second position in which the cavities C and apertures 22 are aligned to allow the material to be sampled by entering and completely filling the exposed cavities C as shown in FIGS. 4 and 5. It is important to note here that the apertures 22 are dimensioned such that they are smaller than the dies 10, 84, to hold the dies securely in place inside the hollow tubular casings 18, 20 when the cavities C and the apertures 22 are aligned to receive samples. This closeness of fit may be ensured by the utilization of springs 80 beneath each die 10 as illustrated in FIG. 4. The handle 24 or 88 is then used to rotate the dies 10 or 84 and die receiving rods 14, 16 or 48, 56 back to the first position to close the sampling apertures for the removal of the device from the sampling area. Thus, precise volumes are obtained within the various cavities C, and dies 10 or 84 are easily removed from the die receiving rods 14, 16 or 48, 56 for testing.

FIG. 6 illustrates a fourth embodiment wherein a single die 92 positioned in cavity D in the hollow die receiving rod 94 has sampling cavities C which are located 180 degrees from each other. The cavities C having equal volumes are exposed one at a time at the same depth by rotation of the receiver handle 180 degrees.

Figure 7:
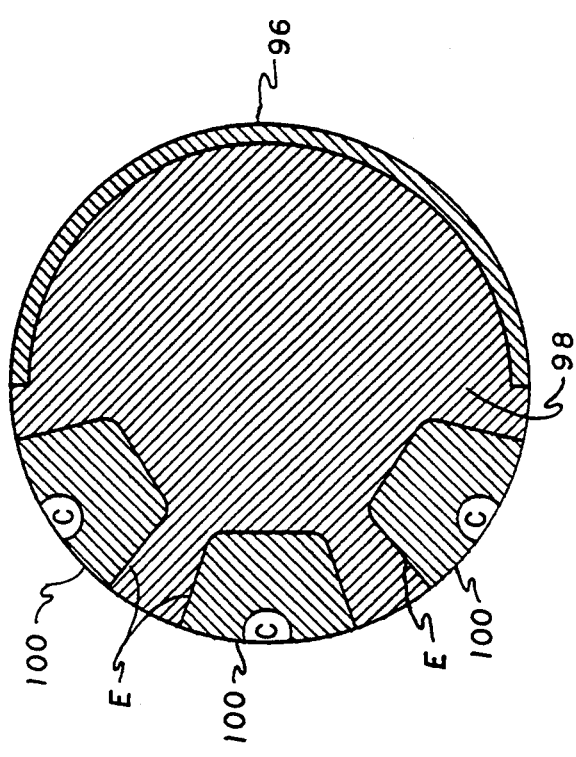
FIG. 7 is a cross-sectional detail view of the fifth embodiment of a hollow receiving rod containing a solid multiple die holder in which three dies arranged circumferentially are supported or nested.

FIG. 7 illustrates a fifth embodiment wherein a hollow die receiving rod 96 is loaded with a solid die holder 98 which fills the inner volume and provides for a number of die cavities E. For example, three dies 100, each containing sampling cavities C, are placed in die cavities E and arranged circumferentially to enable multiple sampling at the same depth, but sequentially, by turning the handle of the die receiving rod 96.

Figure 8:
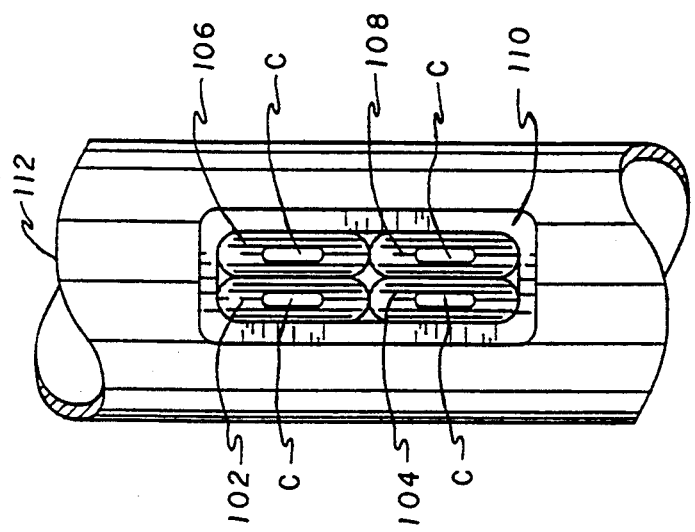
FIG. 8 is a top plan detail view of a sixth embodiment of four dies arranged in a rectangular formation and supported by a die holder in a cavity of a hollow receiving rod having a larger diameter.

FIG. 8 illustrates a sixth embodiment wherein a rectangular die arrangement is utilized preferentially with a sampler having a relatively large two-inch diameter. Four dies 102, 104, 106, and 108 are placed together in a multiple die holder 110 confined in a hollow die receiver 112. The rectangular set of four dies is exposed one at a time through a single aperture 22 in the tubular casing by utilizing the groove or slot 13 (FIG. 1), and manipulating the apparatus as explained previously in the operation of the sampler in FIGS. 1–3. Positioning dips (not shown) in the groove 13 may be included in this embodiment to insure proper positioning for filling each sampling die sequentially. The sampling cavities C are of equal volumes enabling sampling at one location and in four different time periods.

The tubular casing is preferably stainless steel. The receiving rod is preferably solid or tubular stainless steel, or is made from a synthetic material such as a fluorinated polymer resin, commercially available as TEFLON (®), or an acetal polymer resin, commercially available as DELRIN (®). The dies and die holders may be either steel, TEFLON (®) or DELRIN (®). When the length of the sampling device increases, it is preferable to utilize plastic materials.

Retrieval of a long sampling device according to the present invention from the sampling area may be accomplished according to the room available above the mixing vessel. If there is adequate room, no dismantling would be necessary. Dismantling may be performed in disengaging several connected segments at a time.

In summary, the objectives of obtaining accurate volumetric samples at either the same or different depths and at either the same or delayed time period at the same depth of the mixture being sampled, are obtained by the use of this sampling device as well as the facility of utilizing different dies in selected receiving rod segments in the same device.

It is to be understood that the present invention is not limited to the embodiments described above, but encompasses any and all embodiments within the scope of the following claims.

I claim:

1. A multiple-sample sampling device capable of extension for taking multiple samples having accurate volumes from the same area and at different depths of powder or semi-solid mixtures, comprising:
at least a first tubular casing segment and a second tubular casing segment of predetermined lengths, each said first tubular casing segment and said second tubular casing segment having means defining at least one aperture, said first tubular casing segment having a first engaging means at its distal end and a second engaging means at its proximate end, said second tubular casing segment having cooperating engaging means at its distal end for connection to said second engaging means and a grooved pattern at its proximate end;
at least a first die receiving rod segment and a second die receiving rod segment of predetermined lengths, said first die receiving rod segment and said second die receiving rod segment fitting snugly inside said first tubular casing segment and said second tubular casing segment, respectively, said first die receiving rod segment having a third engaging means at its proximate end, said second die receiving rod segment having cooperating engaging means at its distal end for connection to said third engaging means and a handle and pin at its proximate end;
each said first die receiving rod segment and said second die receiving rod segment having means defining at least one first cavity which is aligned with and of greater dimensions than said at least one aperture formed in each of said first tubular casing segment and second tubular casing segment;
at least one die fitting snugly in said at least one first cavity and having at least one second sampling cavity of predetermined sampling volume; and
a solid cone having a fifth engaging means at its proximate end which engages with said first engaging means and closes the distal end of said first tubular casing segment; whereby
said second die receiving rod segment of the sampling device having the handle and pin at its proximate end enables the rotation of said first receiving rod segment and said second receiving rod segment and guides the pin with respect to said grooved pattern of said second tubular casing, thereby aligning and misaligning said at least one die with said at least one aperture in said first tubular casing and said second tubular casing to provide for sampling and discontinuing sampling.

2. The multiple-sample sampling device according to claim 1, wherein said first die receiving rod segment and said second die receiving rod segment are solid.

3. The multiple-sample sampling device according to claim 1, wherein said first die receiving rod segment and said second die receiving rod segment are hollow.

4. The multiple-sample sampling device according to claim 3, further including at least one die-holder which accommodates multiple dies arranged circumferentially.

5. The multiple-sample sampling device according to claim 3, further including at least one die-holder which accommodates a rectangular arrangement of multiple dies.

6. The multiple-sample sampling device according to claim 1, wherein said first receiving rod segment includes two dies arranged longitudinally in said at least one first cavity, said two dies being exposed sequentially by said at least one aperture in said first tubular casing segment.

7. The multiple-sample sampling device according to claim 1, wherein said at least one second sampling cavity includes two said sampling cavities oriented at 180 degrees to each other.

8. The multiple-sample sampling device according to claim 1, comprising at least one spring provided for at least one die, contacting a bottom surface thereof, and urging said die against said at least one tubular casing.

9. The multiple-sample sampling device according to claim 1, comprising at least one blank die to block at least one said sampling aperture.

10. The multiple-sampling device according to claim 1, wherein said third engaging means of said first die receiving rod segment and said cooperating engaging means of said second die receiving rod segment comprise at least one socket connection.

11. The multiple-sample sampling device according to claim 1, wherein said second engaging means of said first tubular casing segment and said cooperating engaging means of said second tubular casing segment comprise key and slot connections secured by a union nut.

12. A method of sampling either a blended pharmaceutical, food or cosmetic mixture in either powder or emulsion form by the use of a segmented sampling device, comprising:

positioning into said blended pharmaceutical, food or cosmetic mixture in either powder or emulsion form, a first sampling device segment comprising a first tubular casing segment closed at its distal end, including aligned apertures from said distal end to a proximate end, and containing dies providing cavities of varying sampling volumes situated in a first receiving rod segment aligned to correspond with said apertures but initially offset to prevent sampling;

inserting at least one second die receiving rod segment containing dies providing cavities of varying sampling volumes into a second tubular casing by coupling with said first rod segment, said second rod segment containing dies aligned with said dies in said first die receiving rod segment, and inserting said second sampling segment further into said powder or emulsion;

attaching a handle to the last sampling segment's die receiving rod, turning the handle to rotate said coupled die receiving rods, to expose said dies providing cavities of varying volumes to said pharmaceutical, food or cosmetic mixture in either powder or emulsion form, and taking precise sample volumes of said powder or emulsion into each die; and turning the handle to rotate the connected die receiving rod segments to close off the apertures in said tubular casing segments.

13. The method of claim 12, comprising the use of solid die receiving rod segments.

14. The method of claim 12, comprising the use of hollow die receiving rod segments.

15. The method of claim 12, comprising the step of placing two dies in communication with at least one aperture and sampling in sequence.

16. The method of claim 13, further comprising the step of providing at least one die with separate sampling cavities located 180 degrees offset from one another, and positioned to take samples in sequence at the same depth.

17. The method of claim 12, further comprising the step of placing at least one blank die lacking sample taking cavities in at least one sampling cavity of said die receiving rod segments to block at least one aperture.

18. The method of claim 12, further comprising the step of grouping together four sampling dies in a rectangular formation in one cavity of the die receiving rod and filling each sampling cavity in sequence.

19. The method of claim 12, further comprising the step of providing within a hollow die receiving rod, at least one die holder which contains at least 3 sampling dies, each die having a sampling cavity, locating said 3 dies circumferentially and equidistantly from one end of the hollow die receiving rod, and filling each sampling cavity in sequence.

* * * * *